United States Patent [19]
Chen et al.

[11] Patent Number: 5,402,779
[45] Date of Patent: Apr. 4, 1995

[54] METHOD FOR THE NON-INVASIVE DETECTION OF AN INTRAVASCULAR INJECTION OF AN ANESTHETIC BY THE USE OF AN INDICATOR DYE

[76] Inventors: William X. Chen, 409 S. Humphrey, Oak Park, Ill. 60302; Charles E. Laurito, 1221 Greenwood Ave., Wilmette, Ill. 60091

[21] Appl. No.: 254,957

[22] Filed: Jun. 7, 1994

Related U.S. Application Data

[63] Continuation-in-part of Ser. No. 238,683, May 5, 1994, abandoned, which is a continuation-in-part of Ser. No. 236,220, Apr. 29, 1994, abandoned.

[51] Int. Cl.⁶ .............................................. A61B 5/00
[52] U.S. Cl. .................... 128/633; 128/664; 128/665
[58] Field of Search ............... 128/633, 634, 664–666, 128/897, 898, 653.1

[56] References Cited

U.S. PATENT DOCUMENTS

| | | |
|---|---|---|
| 3,647,299 | 3/1972 | Lavallee . |
| 4,167,331 | 9/1979 | Nielsen . |
| 4,694,833 | 9/1987 | Hamaguri . |
| 4,776,339 | 10/1988 | Schreiber .......................... 128/633 |
| 4,832,484 | 5/1989 | Aoyagi et al. . |
| 4,877,034 | 10/1989 | Atkins et al. .......................... 128/664 |
| 4,948,248 | 8/1990 | Lehman . |
| 5,178,151 | 1/1993 | Sackner . |
| 5,190,040 | 3/1993 | Aoyagi . |
| 5,218,207 | 6/1993 | Rosenthal . |
| 5,257,972 | 11/1993 | Gurmacnik .......................... 128/898 |

OTHER PUBLICATIONS

Abstract-Microwave Medical Systems Inc.-Exhibit A-date 1987.
Abstract-Acta Anaesthesiol Belg-Exhibit B-1986 vol. 37(1) pp. 59–61.
Abstract-Mocan et al-Can J Anaesth Nov. 1989, 36(6) pp. 708–712.

*Primary Examiner*—Lee S. Cohen
*Assistant Examiner*—Robert L. Nasser, Jr.
*Attorney, Agent, or Firm*—McAndrews, Held & Malloy, Ltd.

[57] ABSTRACT

A method and apparatus in which an anesthesia catheter is inserted into the epidural space of the patient. A blood soluble dye mixed with a local anesthetic is injected through the catheter and into the patient. A transducer clip is positioned on the finger of the patient for monitoring the light responsive characteristics of the patient's blood. A transducer signal is fed to a microprocessor for generating a real time display for indicating to the anesthesiologist that the dye, and therefore the local anesthetic, is present in the bloodstream.

14 Claims, 3 Drawing Sheets

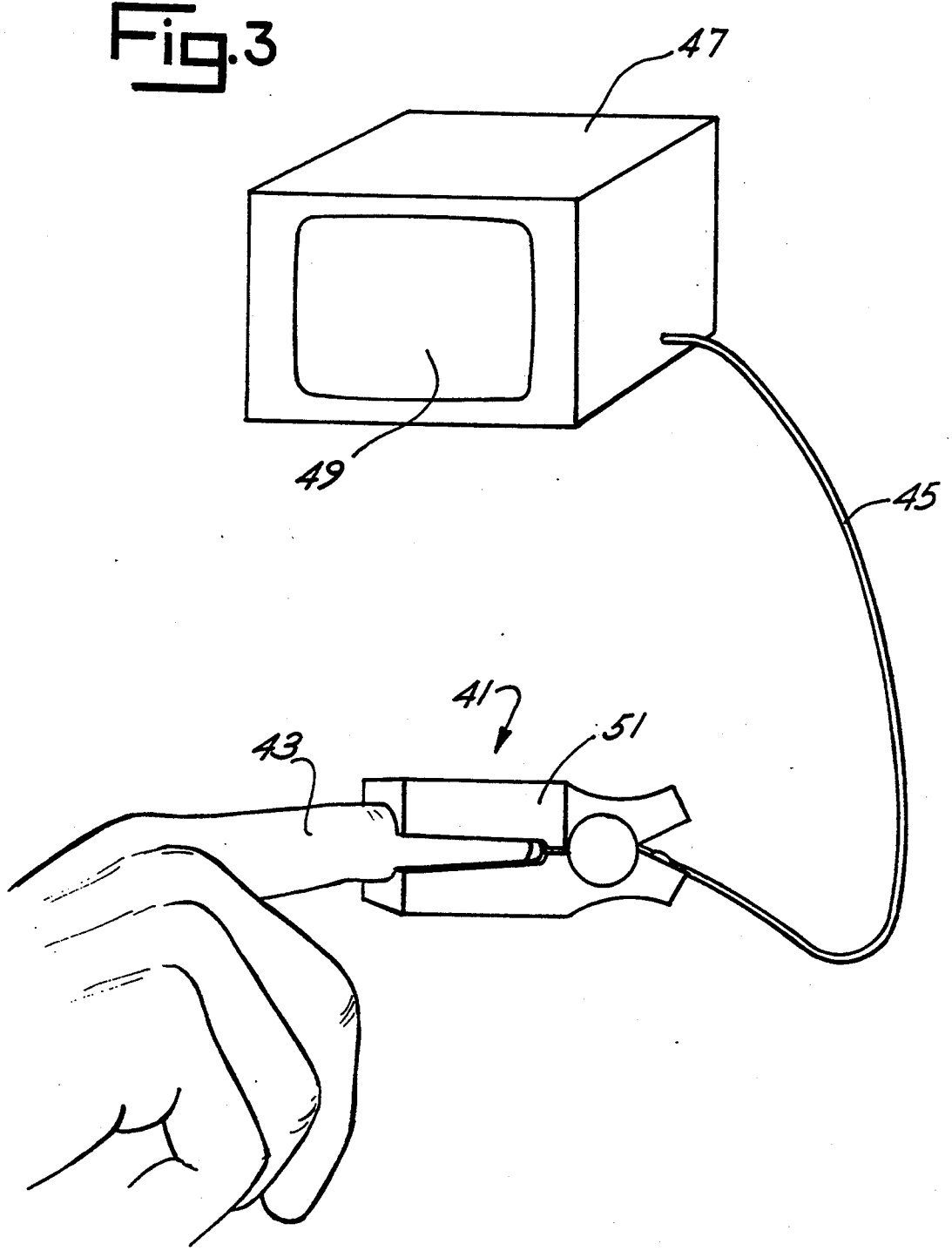

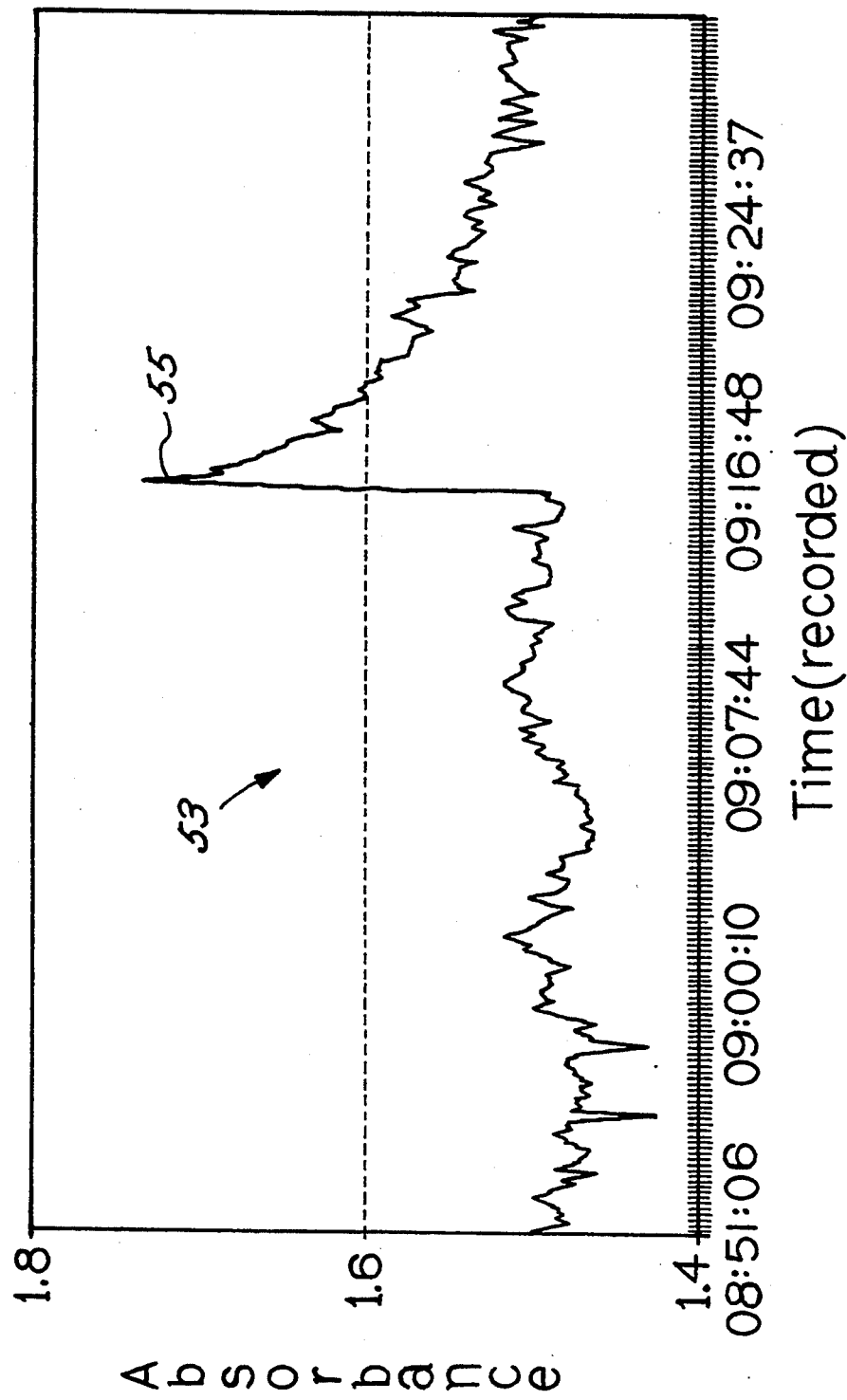

METHOD FOR THE NON-INVASIVE DETECTION OF AN INTRAVASCULAR INJECTION OF AN ANESTHETIC BY THE USE OF AN INDICATOR DYE

CROSS REFERENCE TO RELATED APPLICATIONS

This application is a continuation-in-part of our application Ser. No. 08/238,683, filed May 5, 1994, (now abandoned), which is a continuation-in-part of our application Ser. No. 08/236,220, filed Apr. 29, 1994 (now abandoned).

BACKGROUND OF THE INVENTION

The invention relates to a method and apparatus for non-invasively determining the inadvertent entry of a solution (local anesthetic) through a needle or catheter (conduit) into a blood vessel, and more particularly, to the use of a marker dye which is mixed with the solution and paired with a specific light emitting diode (LED) to allow rapid detection of the substance's appearance in the bloodstream by the detection of an indicator dye.

Anesthesiologists are often called upon to place conduits within the epidural space of patients in order to administer local anesthetics. These medications act directly on nerves as they enter the spinal cord, and render patients insensate to pain. Immediately prior to surgical incisions, these conduits are placed, and the patient is unable to feel the pain from surgical intervention. The technique can also be used in conjunction with general anesthesia. The conduit can be placed before the patient is anesthetized, then local anesthetics are injected during the surgical procedure. This combination of techniques, general and epidural, allows the anesthesiologist to use less general anesthesia than would be used if no conduit were employed. The conduit provides an additional benefit in post operative pain relief. The conduit is left in place with its tip in the epidural space and narcotics and/or local anesthetics are injected/infused to maintain the patient in a pain free state while recovering.

Epidural conduits are often used to care for pregnant women who are experiencing labor pains. The flexible conduit is placed into the appropriate space in a patient's back with its proximal aspect taped to the skin of the back. A continuous infusion of local anesthetic and/or narcotic acts on the nerves as they enter the spinal cord to dull the pain of uterine contraction during labor. If the solution is dilute enough, sensation is decreased while motor strength maintained. The patient is able to assist in the process of labor without the intense pain normally experienced during childbirth.

A problem with the use of this technique is the difficulty in confirming and maintaining correct conduit placement for delivery of the solution to be infused. The epidural space is located deep in the back and is surrounded by many vascular structures. If a conduit tip is accidently placed or is correctly placed but subsequently migrates into a blood vessel, the solution will be injected/infused not into the epidural space, but directly into the bloodstream. If blood levels of local anesthetic rise quickly, the patient will rapidly experience cardiovascular and neurologic complications. This is a very dangerous complication of an otherwise safe technique. The rapid administration of commonly used solutions can cause complications leading to severe morbidity, and, on occasion, mortality.

Many attempts have been made to improve the safety of the technique by mixing anesthetic solutions with other substances and medications which will provide a measurable change that can be detected by the anesthesiologist if the mixture is injected into a blood vessel. These changes can take the form of blood pressure or heart rate increases, detection of air within the vascular space, or an acute change in the patient's mental status. These substances are added in an attempt to detect the intravascular injection of local anesthetic rapidly so the injection can be stopped before medical complications develop. Yet none of the currently used substances and medications are completely reliable. Investigators have used neosynephrine, isoproterenol, chloroprocaine, microbubble preparations, and epinephrine. Epinephrine (epi) is most commonly used as an indicator. It has been used for this purpose since 1981, but it is far from ideal. Epi will not reliably cause a cardiovascular change recognized by the physician. Some people don't react as reliably as do others and the blood pressure or heart rate changes can be so small that they aren't detected by the clinician. Even very small doses of epi injection into the bloodstream have the potential to cause medical complications: hypertension, tachycardia, or bradycardia. At times, these changes are sufficient to cause ischemic changes of the heart muscle leading to arrhythmias or myocardial infarction (heart attack). Epi has also been shown to decrease blood flow from the pregnant woman's heart to her uterus. This change will decrease the flow of oxygen and nutrients to the fetus and, in some instances, put the fetus in jeopardy. Epi has also been shown to give unreliable findings in geriatric patients and in those who are concurrently receiving certain classes of medications, i.e., beta blockers for underlying medical conditions. Microbubble preparations have been made by injecting a small dose of room air into the proximal port on the epidural conduit. If the tip of the conduit is correctly placed in the epidural space, the air is harmlessly absorbed. If the tip is located within a blood vessel, the air is taken up by the blood stream and taken back to the heart. When the air bubble reaches the right atrium and right ventricle, it makes a frothy mixture of air and blood. As the heart continues to beat, this frothy mixture makes a characteristic sound that can be heard if a stethoscope or doppler measuring device is applied to the chest wall. The technique of injecting air into the conduit gives a reliable indication when the conduit tip is within a vessel but also introduces a danger. Although the frothy mixture is usually absorbed by the body with no complications, in some instances, the air can travel through an opening in the right atrium into the left atrium. In these instances, the air travels to the left ventricle and directly to the systemic circulation. If the air happens to travel to the brain, it will displace the blood that should be there and cause a cerebrovascular accident, i.e., a stroke. In addition, the use of air before the use of local anesthetic within the catheter doesn't exclude the possibility that the conduit will migrate into a blood vessel after the injection of air. There is no way to have the air act as a marker for every small amount of local anesthetic that is injected. With each heart beat, the pulsatile force is conducted to vessels in the back. The conduits which are placed in this location are affected by the movement such that the tip of the conduit can erode through the vessel wall and migrate into a blood vessel. An air test showing that the conduit tip is not in a blood vessel may be followed immediately by the injection of local anesthetic into a blood vessel.

A more reliable method is needed in which an immediate warning will occur at anytime during the course of an injection/infusion through the conduit which will alert care givers. This warning will allow corrective action to be taken before local anesthetic levels rise to high levels and cause medical complications.

It is therefore an object of the present invention to provide a means for rapidly and non-invasively determining whether a small dose of the
solution (local anesthetic) has entered a blood vessel.

It is yet another object of the present invention to provide a simple and accurate method for determining whether a conduit to be placed in the epidural space or by another collection of nerves or a nerve has entered a neighboring blood vessel.

It is yet another object of the present invention to provide a blood marker dye which is mixed with a substance such as a local anesthetic and injected near a nerve or a collection of nerves as, for example, into the epidural space, and the presence of this dye monitored non-invasively at a distant site on the patient for rapidly determining improper conduit tip placement by entry of the solution and indicator dye into the blood stream.

SUMMARY OF THE INVENTION

These and other objects of the invention are achieved in a method and apparatus for determining improper anesthetic conduit placement. In particular, in one aspect of the invention, a conduit is positioned in the epidural space and an
indicator dye/local anesthetic mixture is injected/infused through the conduit. The patient's blood is non-invasively monitored at a distant site, for example, the fingertip, to determine if the dye and therefore the local anesthetic has inadvertently entered the blood stream directly. This invention will allow the early detection of a dye which was previously mixed with a substance (local anesthetic) within the blood stream before high levels of local anesthetic cause medical complications for the patient.

Non-invasive detection of the dye at a distant site of the body will indicate vascular injection of the dyelocal anesthetic mixture as can follow improper conduit placement.

BRIEF DESCRIPTION OF THE DRAWINGS

FIG. 3 is a diagrammatic representation of the blood monitoring apparatus for use in connection with the present invention.

FIG. 4 is a graphical representation of a display generated by the apparatus of FIG. 3.

DETAILED DESCRIPTION OF THE PREFERRED EMBODIMENT

Figure 1:
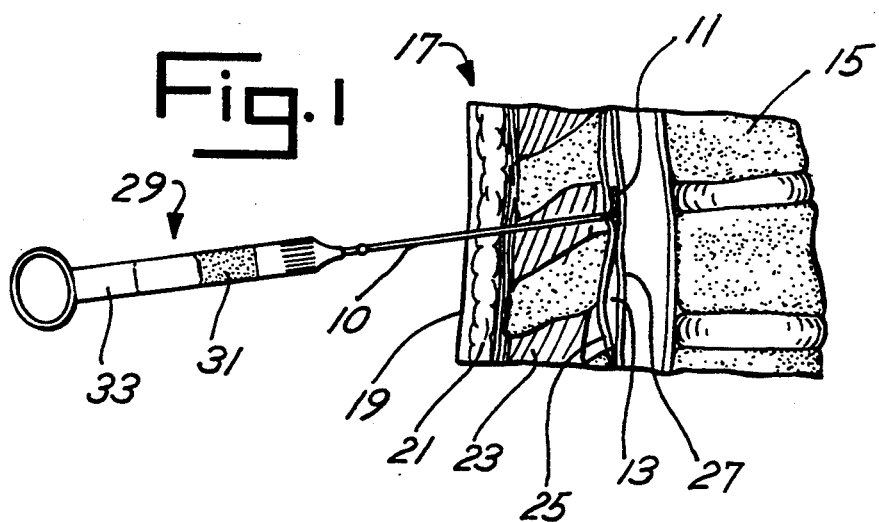
FIG. 1 is a partial cross-sectional side view of the patient's spinal area illustrating placement of an anesthesia needle and catheter, for use in accordance with the present invention.

Referring to FIG. 1, epidural anesthesia is provided using a relatively long conduit, for example, a needle 10, which is inserted into the epidural space 13 of the spine area 15 of a patient, generally indicated by reference numeral 17. Needle 10 initially passes through outer skin 19, subcutaneous fat 21, ligaments 23 and through the ligamentum flavum 25. The epidural space 13 lies between the ligamentum flavum 25 and the dura 27.

Needle 10 is hollow, being formed of a rigid metal shaft. As understood, a syringe 29 may be attached to the needle for injecting a liquid directly into the epidural space. However, typically a flexible, plastic, hollow conduit, for example, a catheter 11 is threaded inside needle 10 and pushed out into epidural space 13, once the needle has been inserted into position. Thereafter, the rigid needle 10 is removed leaving only the flexible catheter 11 in position.

After the catheter is in place, a syringe 29 is attached to the catheter. An anesthetic solution 31 is forced by the syringe plunger 33 through catheter 11 and into epidural space 13. The anesthetic solution may be chosen from, for example, conventional drugs available for epidural use, as understood. As also understood, a supply (not shown) of anesthetic solution may be placed in an infusion device (not shown) which is attached to catheter 11 for providing continuous infusion of the solution. As also understood, the rigid needle 10 alone, without catheter 11, may be used to inject the anesthetic solution.

Figure 2:
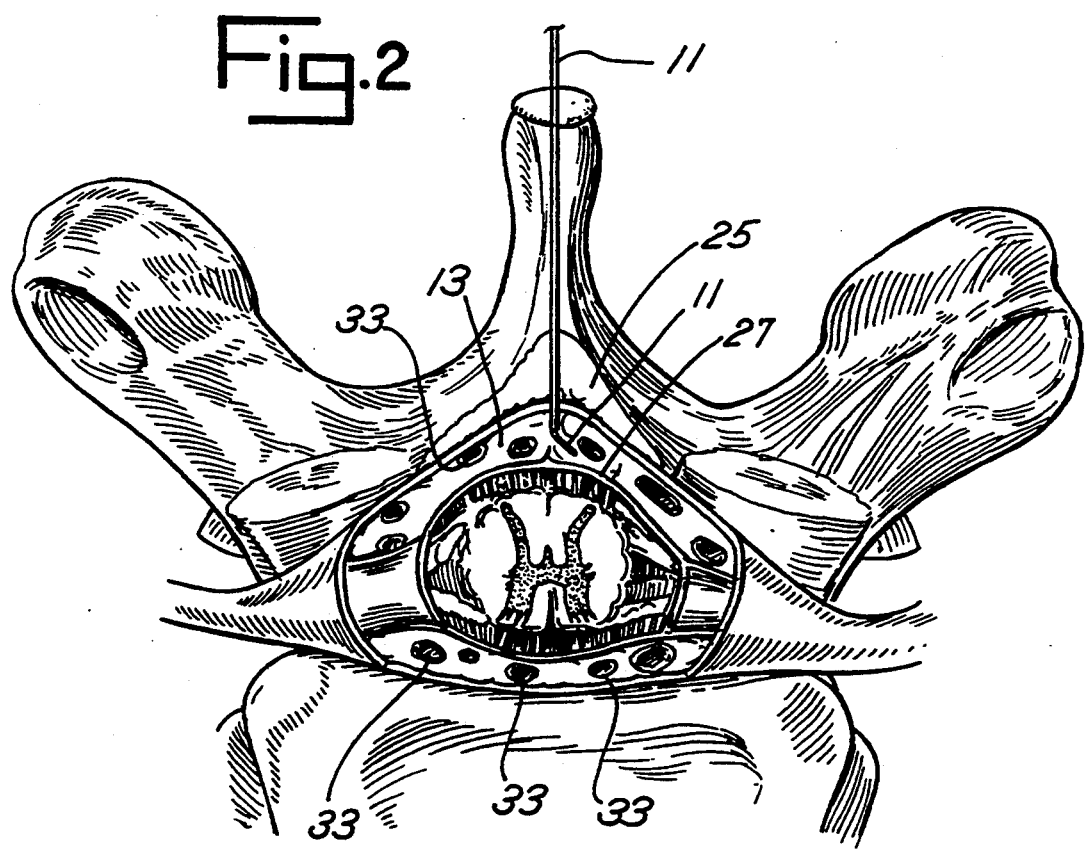
FIG. 2 is a cross-sectional top view of the spinal area of FIG. 1.

Referring to FIG. 2, the epidural space 13 includes a plurality of blood vessels 33. It is important that catheter 11 does not enter or migrate within a blood vessel 33. Systemic toxicity resulting from a large intravenous injection of the intended epidural anesthetic dose could occur.

In order to detect whether the conduit has entered a blood vessel, a dye or a mixture of a dye with a local anesthetic ("dye/local anesthetic") is injected immediately after catheter placement. If
the conduit has inadvertently entered a blood vessel, the dye or dye/local anesthetic passes into the patient's bloodstream. Non-invasive detection of the dye at a distant site of the body will indicate vascular injection of the dye/local anesthetic mixture as can follow improper catheter placement.

The dye may be five to ten milliliters of 0.5% indocyanine green (up to a maximum dose of 0.5 mg/kg). Indocyanine green ("ICG") is a sterile, water soluble, tricarbocyanine dye having a maximum spectrophotometric absorption peak of from 800 to 810 nm in blood or plasma.

The dose of the ICG dye is selected so as to be large enough to cause a significant change in the spectrometry reading of the blood. Also, the dose is kept small enough for practical use as an injectate, and so as not to appreciably dilute the effect of the local anesthetic, and so that adverse reactions, if any, are not likely to occur.

The biological dye ICG is available in a powdered form and must be prepared as a solution. The dye may be mixed with sterile water and then mixed with the liquid anesthetic to form the dose. Once mixed, the solution should be used within 10 hours. A protein, albumin, may be mixed with the dye solution in order to prolong the optical stability of the dye. Specifically, a stabilizer may be added to the dye in order to prolong the spectral absorption of light by the dye.

The ICG dye has been used since the 1940's and has been shown to be safe when injected intravascularly. Its presence within the blood stream is detected at a distant site by the use of spectrophotometric equipment.

Referring to FIG. 3, a non-invasive transducer 41 is positioned over the patient's finger 43. Transducer 41 is in the form of a spring biased clip 51. A light source, for example, a light emitting diode LED (not shown), is housed in clip 51 and transmits light of a specific wavelength through the finger and onto a photosensor, for example, a photodiode (not shown).

The wavelength of the light generated by the LED corresponds to an absorption peak of the particular indicator dye used. In the case of indocyanine green (ICG), the wavelength is 800-810 nanometers. At baseline, the photodiode will detect light emitted by the LED and generate an electrical signal proportional to the intensity of light transmitted through the finger. If the dye or the dye/local anesthetic enters the blood stream, it will be carried to the distant site where it will interfere with the transmission of light through the finger by decreasing the intensity of the transmitted light. In turn, the photodiode will generate an electrical signal of diminishing amplitude indicating the presence of the ICG dye. This change in the electrical signal will be visually or audibly displayed to the anesthesiologist or other medical worker.

A conductor 45 carries an electrical signal representative of light transmissivity of the blood, as indicated by the output of the photodiode. The electrical signal is fed to a microprocessor based analyzer 47 which analyzes the data carried by, the electrical signal i.e., the amplitude. The amplitude is proportional to the amount of light reaching the photodiode.

A monitor display screen 49 shows the results of the analysis. The analysis may be used to generate an indicator for clinical use. For example, a warning sound, a color change, a visual flashing light, a cathode ray tube (CRT) line display change, etc. may be generated.

If the dye is correctly injected into the epidural space, no change or only a minor change in the photometric reading is seen. However, if the dye enters the blood circulation directly, the photometric system (41, 45, 47, 49) will detect an immediate and abrupt change as the dye travels back to the heart and is subsequently pumped to the extremity where the light sensor 41 is placed. Presence of the dye in the blood of the extremity will be detected by a change in the intensity of the light reaching the photodetector. This change is highly sensitive because the LED employed generates light of a wavelength which corresponds to a peak absorption of the specific dye used as an indicator.

As shown in FIG. 4, display screen 49 shows a graph 53 of the light absorbance of the blood in the patient's finger with respect to time. The change in the intensity of the transmitted light is detected by sensor 41 at time 09:16:48, as shown by the large spike 55 on graph 53. This wave spike 55 serves as a visual indicator to the anesthesiologist that the catheter 11 through which the local anesthetic/dye mixture is injected has entered a blood vessel.

This indication may be converted to another form, for example, a displayed number, shape, color change or audio alarm. Upon warning from the indicator, the anesthesiologist will know to move the needle or catheter tip from its improper site in a blood vessel to a proper location in the epidural space or to an appropriate location by a nerve or group of nerves.

What is claimed is:

1. A method for use by an anesthesiologist for non-invasively determining whether an anesthetic has inadvertently entered a blood vessel of a patient, comprising:

inserting an anesthesia catheter into the body of a patient;
   preparing a blood soluble dye having light absorption characteristics and characteristics which permit its flow within the bloodstream of the patient;
   injecting the blood soluble dye through the catheter and into the patient;
   non-invasively monitoring the patient's blood at a location remote from the catheter, said monitoring detecting a change in transmitted light through the blood to sense the presence of the dye in the bloodstream; and
   indicating to the anesthesiologist that the dye has been sensed in the bloodstream by said step of monitoring.

2. A method according to claim 1 wherein said step of monitoring includes transmitting light of a wavelength related to said light absorption characteristics of said dye through the patient's blood.

3. A method according to claim 2 wherein said step of monitoring includes sensing the intensity of light transmitted through the patient's bloodstream.

4. A method according to claim 1 wherein said step of monitoring includes securing a transducer at the fingertip of the patient's finger.

5. A method according to claim 1 wherein said step of inserting the catheter includes positioning an end of the catheter in the epidural space of the patient.

6. A method according to claim 1 wherein said step of preparing the dye includes mixing a powdered dye with sterile water.

7. A method according to claim 1 wherein said step of preparing the dye includes adding a stabilizer.

8. A method according to claim 1 wherein said step of preparing the dye includes mixing the dye with an anesthetic; and wherein said step of injecting the dye includes injecting the mixed dye and anesthetic.

9. A method according to claim 8 wherein said step of injecting the mixed dye and anesthetic includes continuous infusing of the mixed dye and anesthetic throughout a period of time.

10. A method according to claim 1 wherein said step of injecting the dye includes placing a dye in a syringe; and fixing the syringe to the catheter.

11. A method according to claim 1 wherein said step of indicating includes generating an audible alarm.

12. A method according to claim 1 wherein said step of indicating includes displaying a graph of a real time monitoring of the patient's blood.

13. A method according to claim 12 wherein said step of indicating includes visually displaying the real time light absorption characteristics of the bloodstream.

14. A method for use by a medical user for non-invasively determining whether a conduit has inadvertently entered a blood vessel of a patient, comprising:

inserting a conduit into the body of a patient;
   preparing a blood soluble dye having characteristics which permit its flow within the bloodstream of the patient;
   injecting the blood soluble dye through the conduit and into the patient;
   non-invasively monitoring the patient's blood at a location remote from the conduit to sense for the dye in the bloodstream; and
   indicating to the medical user that the conduit has inadvertently entered a blood vessel because the dye has been sensed in the bloodstream by said step of monitoring.

* * * * *